United States Patent [19]

Strimel

[11] Patent Number: 4,624,144

[45] Date of Patent: Nov. 25, 1986

[54] FOR TESTING MACHINES, IMPROVEMENTS IN DETERMINING RUPTURE POINT AND SETTING GAUGE LENGTH

[75] Inventor: Robert S. Strimel, Penllyn, Pa.

[73] Assignee: Tinius Olsen Testing Machine Co., Willow Grove, Pa.

[21] Appl. No.: 613,359

[22] Filed: May 23, 1984

[51] Int. Cl.[4] .............................................. G01N 3/08
[52] U.S. Cl. ...................................... 73/834; 73/826
[58] Field of Search ................ 73/799, 830, 831, 834, 73/826, 828, 855, 856, 857, 860, 862.39, 862.42, 810, 816, 763, 768, 774, 845, 848, 851, 1 R, 1 J; 33/147 D, 148 D, 143 M, 143 K, 168 B; 340/668 (U.S. only); 269/254 R, 254 LS, 286, 238, 258, 93, 94

[56] References Cited

U.S. PATENT DOCUMENTS

| | | | |
|---|---|---|---|
| 615,071 | 11/1898 | Ledward | 269/258 |
| 1,499,989 | 7/1924 | Lehmann | 269/254 LS |
| 2,611,966 | 9/1952 | Rebman | 33/148 D |
| 2,814,883 | 12/1957 | Strimel | 73/779 |
| 2,845,828 | 8/1958 | Thomeczek | 269/258 |
| 3,287,964 | 11/1966 | Dennis | 73/830 |
| 3,600,939 | 8/1971 | Steele | 33/147 D |
| 3,721,119 | 3/1973 | Strimel | 73/816 |
| 3,835,699 | 9/1974 | Strimel | 73/774 |

FOREIGN PATENT DOCUMENTS 555801 9/1943 United Kingdom ................ 269/261

OTHER PUBLICATIONS

Strimel, "Automated Horizontal Tensile Testing Machines for Rapid Quality Control Testing", Journal of Metals, Jul. 1980.

Primary Examiner—Stewart J. Levy
Assistant Examiner—Robert R. Raevis
Attorney, Agent, or Firm—Frederick J. Olsson

[57] ABSTRACT

A tensile testing machine has a pair of cross heads relatively movable along an axis, each cross head having a mechanism for fixedly holding one end of an electrically conductive specimen and in at least one of said mechanisms, electrical insulating means electrically isolating the end of the specimen from the mechanism to provide for the specimen to be part of an electrical circuit for determining the time of specimen rupture. The testing machine also has an extensometer including a pair of strain followers with improved means for setting the gauge length of the strain followers which comprises a pair of gauge followers respectively connected to the strain followers and each gauge follower having an exterior concave groove, a pair of gauge cams, and means supporting the gauge cams a fixed distance apart and for a reciprocating motion toward and away from the gauge followers to respectively engage with and to disengage from the exterior concave grooves, the engagements being for use in establishing the gauge length of the strain followers.

5 Claims, 9 Drawing Figures

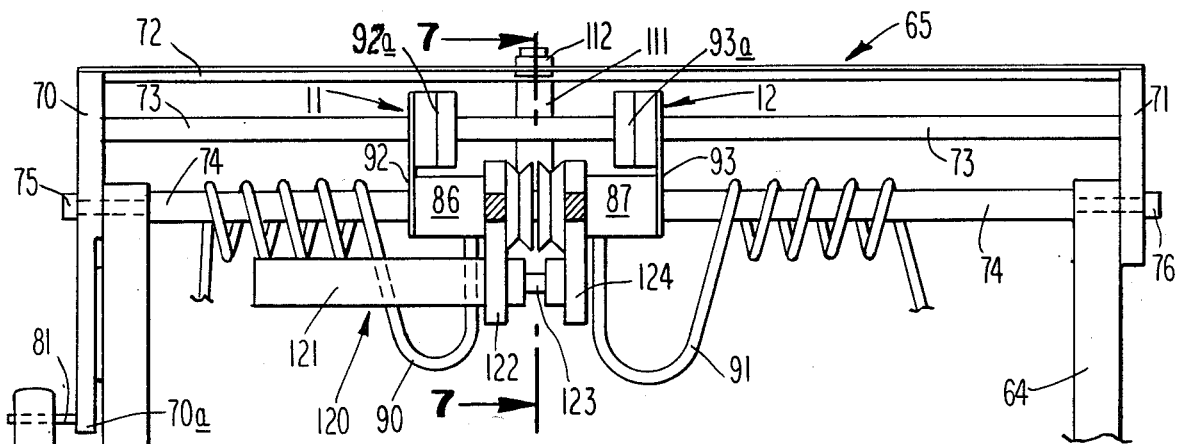
Fig. 6
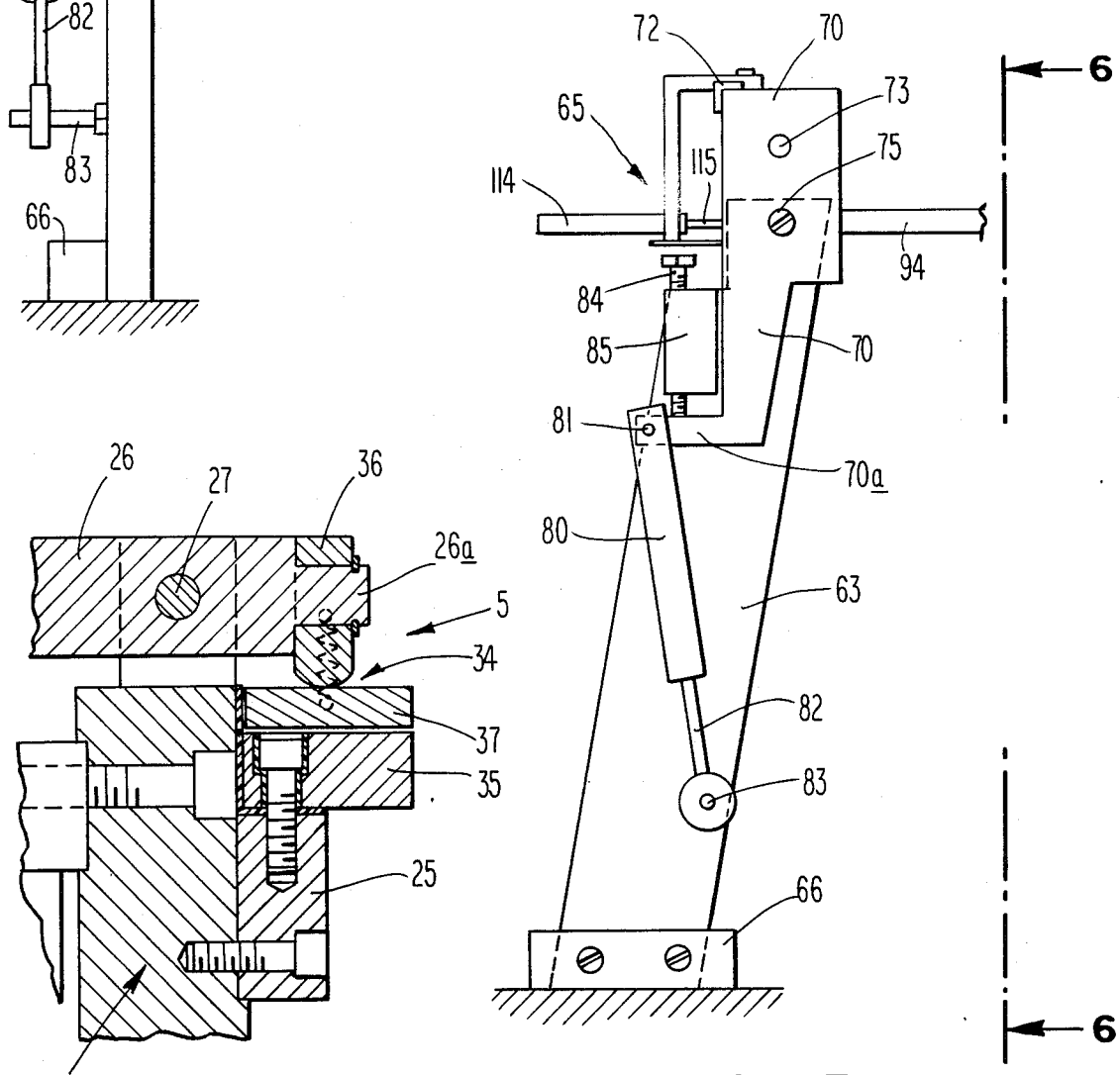
Fig. 9
Fig. 5

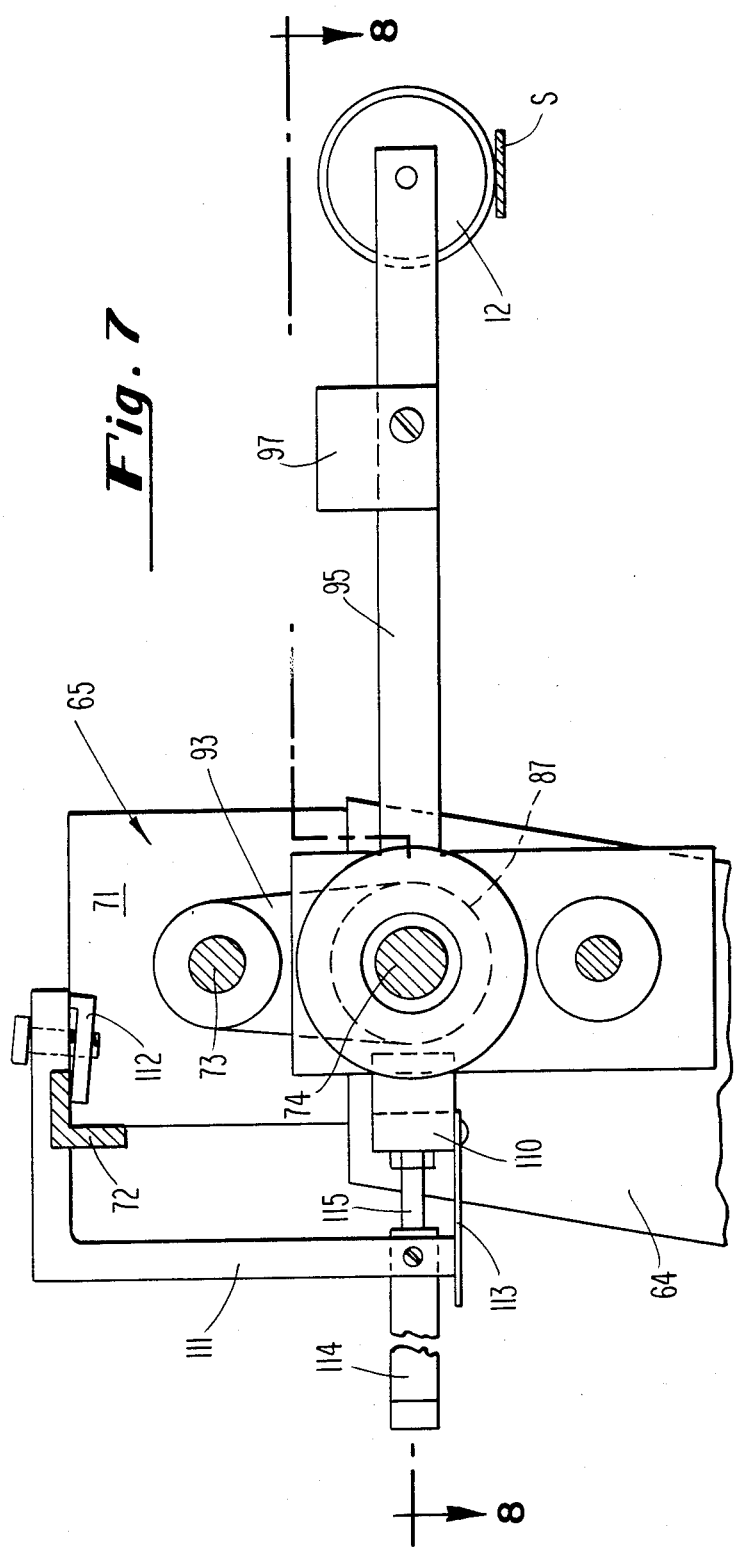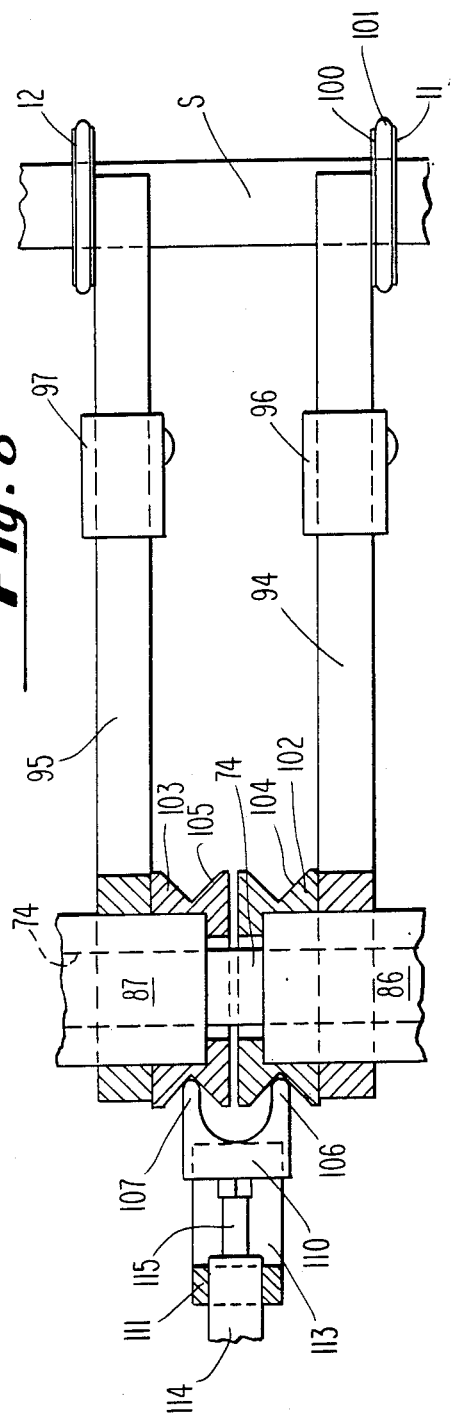

FOR TESTING MACHINES, IMPROVEMENTS IN DETERMINING RUPTURE POINT AND SETTING GAUGE LENGTH

This invention in general relates to physical testing machines of the kind adapted to apply tensile forces to specimens and in particular relates to improved means for mounting a specimen so that the exact point of rupture can be determined and to an improved extensometer which automatically sets the gauge length of the strain followers.

One of the objectives of the invention is to promote the useful art of physical testing by providing specimen gripping means which permit an electrically conductive specimen to be part of an electrical circuit during the testing period so that upon rupture the circuit is interrupted and, thus, accurately indicate the rupture point.

Another of the objectives of the invention is to promote the useful art of physical testing by providing an extensometer wherein the gauge length of the strain followers can be automatically and accurately set.

While the invention will be explained in connection with a horizontal testing machine, the application of the invention to vertical testing machines will be readily apparent to those skilled in the art.

Various features and advantages of the invention will be readily apparent to those skilled in the art of physical testing by reference to the following specification taken in conjunction with the accompanying drawings forming a part thereof, it being understood that modifications may be made in the structural details shown and described herein and as set forth in the appendent claims without departing from the spirit and scope of the invention.

FIG. 5 is an enlarged elevational view and view of the extensometer of the invention as taken along the lines 5—5 of FIG. 4.

FIG. 6 is an elevational view of the components of FIG. 5 taken along the lines 6—6 of this figure.

FIG. 7 is an enlarged fragmentary elevational view taken along the lines 7—7 of FIG. 6.

FIG. 8 is a plan view taken along the lines 8—8 of FIG. 7. and

FIG. 9 is a cross-sectional elevational view of the improved specimen clamping means of the invention.

Figure 1:
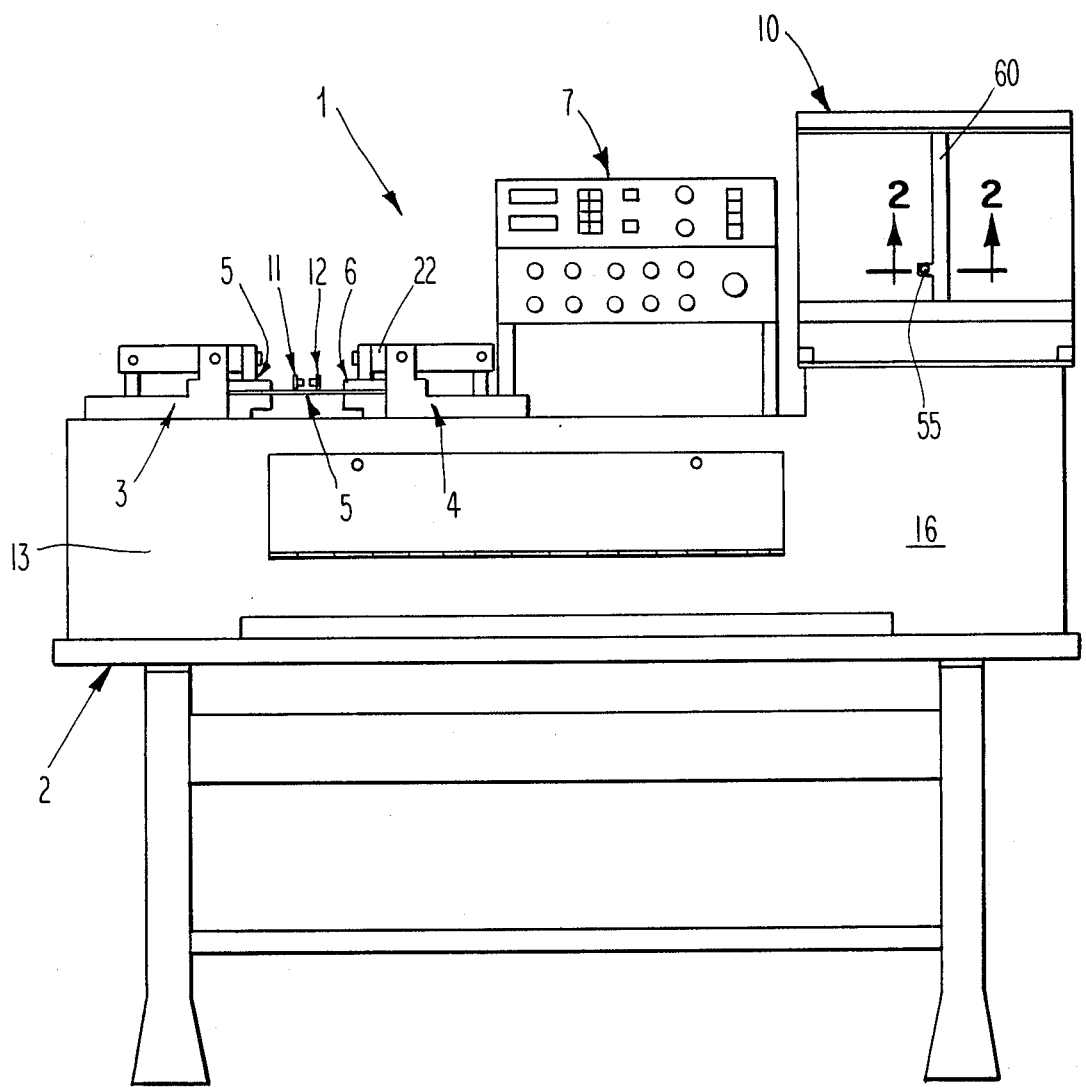
FIG. 1 is a front elevational view of a horizontal testing machine embodying the invention.

In FIG. 1 a horizontal testing machine 1 for tension testing a specimen S includes a frame 2, fixed cross and movable cross heads 3 and 4 between which the specimen S is clamped for testing by the specimen clamping means 5 and 6, a control module 7, and X-Y type recorder 10, an extensometer whose strain followers are indicated at 11 and 12, together with a cross head loading system and a load measuring or weighing system inside the housing 13.

Figure 3:
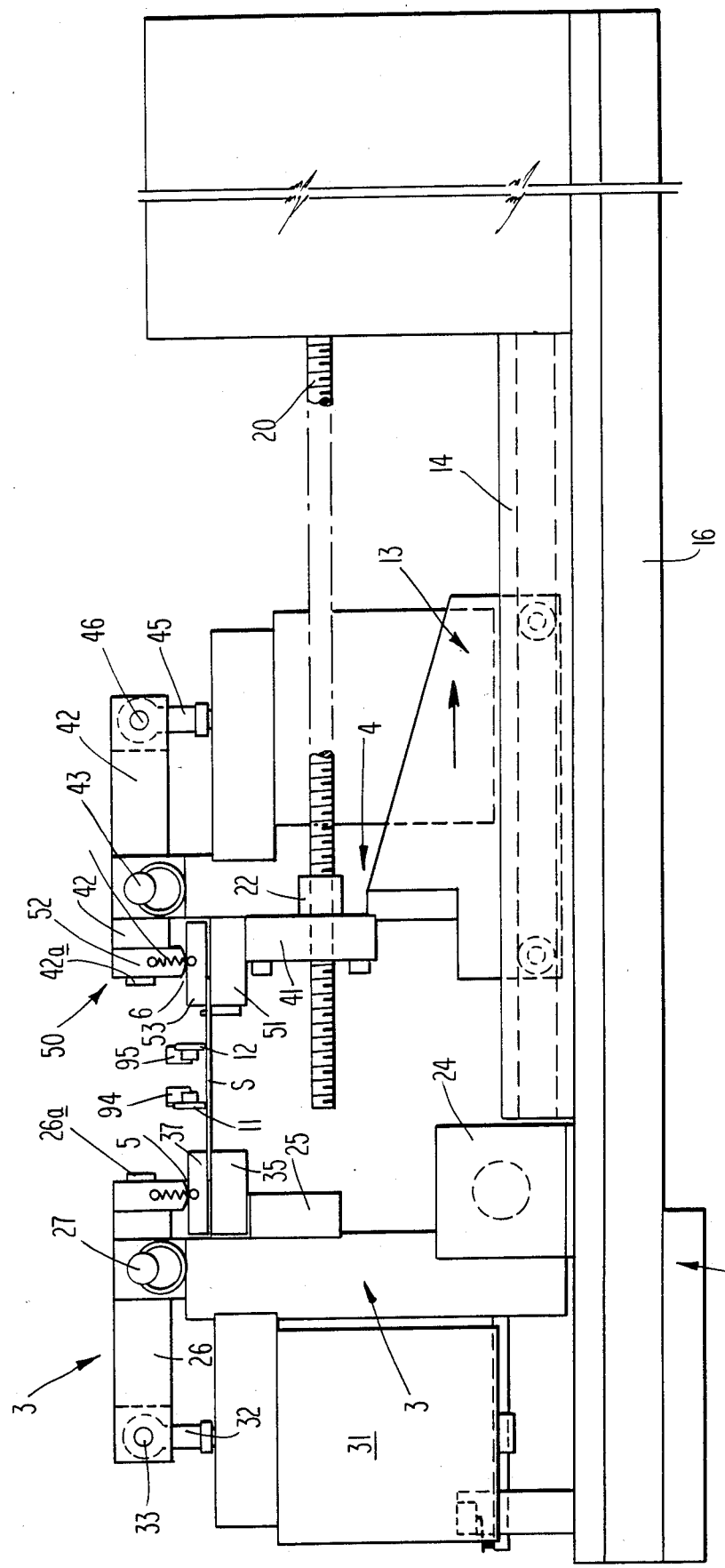
FIG. 3 is an enlarged front elevational view illustrating the loading, weighing, and specimen clamping systems of the machine of FIG. 1.
Figure 4:
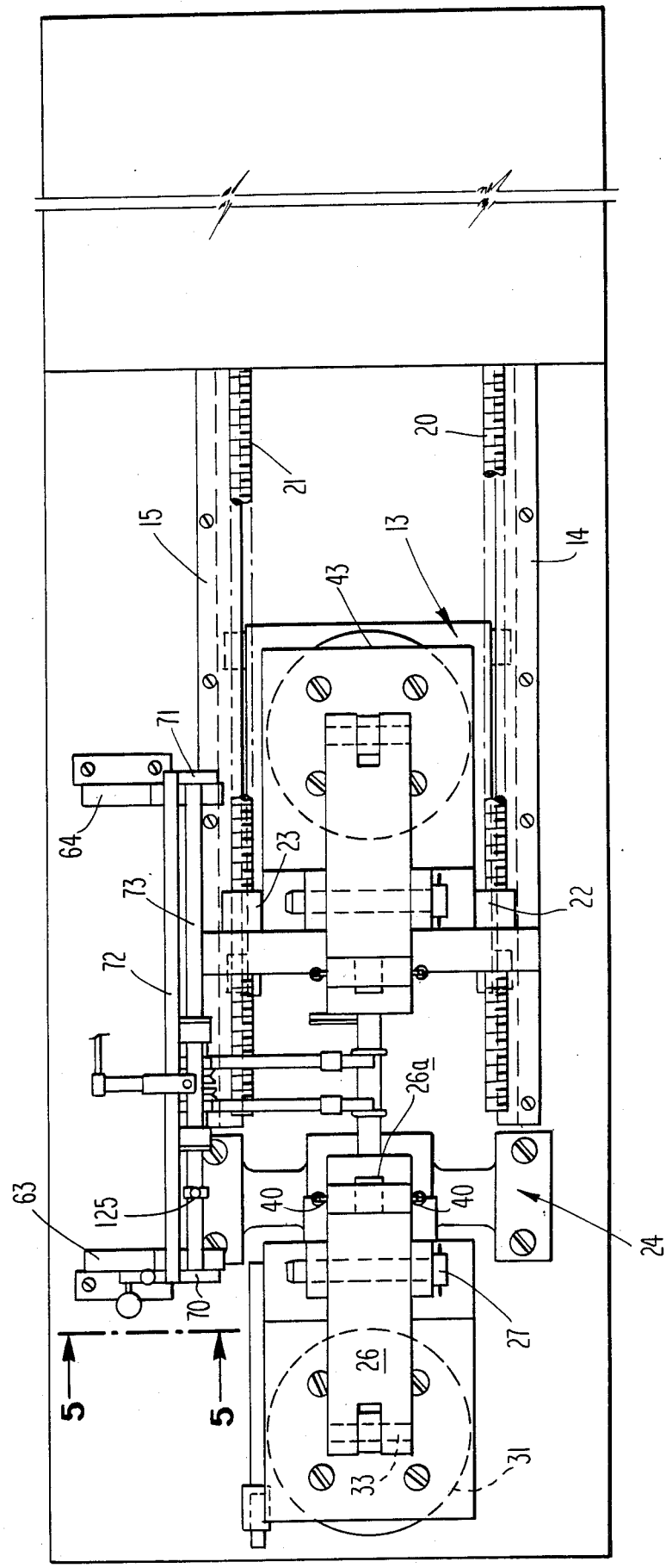
FIG. 4 is a plan view of the components illustrated in FIG. 3.

Referring to FIGS. 3 and 4 I will briefly describe a typical loading system for the above machine.

A carriage 13 is roller supported on the guides 14 and 15 fixed on the base 16 and mounts the movable cross head 4. A pair of lead screws 20 and 21 operate in nuts 22 and 23 on the carriage 13 and are adapted to be rotated by a drive mechanism (not shown). Rotation of the lead screws will cause the carriage 13 to move (left or right) along the guides 14 and 15 and, thus, move the movable cross head 4 toward and away from the fixed cross head 3. Movement of the cross head 4 away from the cross head 3 puts the specimen in tension. The control module 7 has means for controlling the rate of motion of the carriage 13.

The fixed cross head 3 is mounted on the load measuring or weighing system which is of the torque bar type, a typical example of which is shown in U.S. Pat. No. 3,721,119. Thus, the cross head 3 is mounted on the torque bar 24 fixed to the base 16. As the specimen is put into tension, the torque bar tends to twist or yield so that the cross head 3 is tilted slightly clockwise as a function of the load on the specimen. The twisting motion of the torque bar is sensed and signals developed to indicate the magnitude of the load. It might be noted here that the cross head 3 is fixed in the sense that it does not move along the base 16 as does the cross head 4 but is capable of slight tilting motion as just noted.

The fixed cross head 3 carries a specimen support mechanism 25 and specimen clamp arm 26 which are employed in connection with the specimen clamping means 5. With reference to FIG. 9, the specimen support mechanism 25 is in the form of a block bolted to the head 3 and the specimen clamp arm 26 is mounted on the cross head by pivot 27 so that its end 26a is movable toward and away from the specimen support mechanism 25.

The specimen clamp arm 26 is moved as by a piston/cylinder, the cylinder 31 being secured to the cross head 3 and the piston inside of the cylinder having a rod 32 pivotally secured to the specimen clamp arm 26 as by pivot 33.

As mentioned heretofore, one of the features of the invention is to mount the specimen in the cross heads so that it may be part of an electrical circuit which is interrupted when the specimen breaks to thereby determine the exact rupture time. This feature will be explained in connection with the description of the specimen clamping means 5 and 6.

First, with reference to FIG. 9, the specimen clamping means 5 comprises specimen clamping head 34 on the arm 26 and specimen clamping platform 35 on the support mechanism 25.

The specimen clamping head 34 comprises the end block 36 mounted on the end 26a of the clamping arm 26, clamp block 37 and springs 40 which urge the blocks into engagement. The lower edge of the block 36 is convex in shape and engages the flat, top side of the clamp block 37. The clamp block can tilt with respect to the end block. The underside of the clamp block 37 is also flat.

When one end of a specimen is positioned between the clamp block 37 and platform 35, clockwise rotation of arm 26 will cause the end of the specimen to be tightly gripped.

In the arrangement described the end block 36 is made of an electrical insulating material preferably nylon and the platform 35 and clamp block 37 are each made of metal. The platform 35 is electrically isolated from the cross head 3 by the insulating material 38 also preferably made of nylon. Thus, it will be apparent that a specimen gripped between the platform 35 and the clamp block 37 is electrically isolated from the cross head 3.

Returning now to the movable cross head 4, (FIG. 3) this cross head carries a specimen support mechanism 41 and a specimen clamp arm 42 which are employed in connection with the specimen clamping means 6.

The specimen support mechanism 41 is in the form of a block bolted to the cross head 4. The specimen clamp arm 42 is mounted on the cross head by pivot 43 so that the end 42a is movable toward and away from the specimen support mechanism 41.

The specimen clamp arm 42 is moved as by a piston/cylinder, the cylinder 43 being secured to the cross head 4 and the piston inside the cylinder having a rod 45 pivotally secured to the arm 42 as by pivot 46.

The specimen clamping means 6 comprises specimen clamping head 50 on the arm 42 and specimen clamping platform 51 and the specimen support mechanism 41.

The specimen clamping head 50 comprises the end block 52 mounted on the end 42a of the clamping arm 42, clamp block 53, and springs 54 which urge the blocks into engagement. The lower edge of the end block 52 is convex in shape and engages the flat, top side of the clamp block 53. The clamp block 53 can tilt with respect to the end block. The underside of the clamp block 53 is also flat.

When an end of a specimen is positioned between the clamp block 53 and the platform 51 counterclockwise rotation of the clamp arm 42 will cause the end of the specimen to be tightly gripped.

The structure just described is identical to the corresponding structure on the cross head 3 except that the end block 52 is metal and the specimen clamping platform 51 is not electrically isolated from the specimen support 41.

Figure 2:
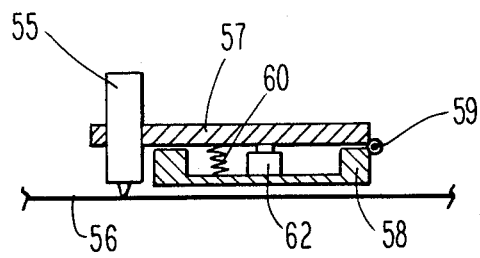
FIG. 2 is an enlarged fragmentary view taken along the lines 2—2 of FIG. 1 and illustrating the recorder pen and means for controlling its contact with the recording chart paper.

It will be apparent that the specimen clamped between the clamping means 5 and 6 can be connected to an electrical circuit via a connection to the cross head 4 and a connection to the clamping platform 35 (or clamp block 37). Therefore, at the instant of specimen rupture, the circuit will be opened. By using conventional circuit components, the opening of the specimen circuit is used to drive indicating and/or control means. For example, to cause the stress/strain curve being plotted by the recorder 10 to be terminated at the point of rupture. Thus, referring to FIG. 2, a recorder pen 55 operates on chart paper 56. During a test the pen 55 engages the chart paper 56 and at the point of rupture the pen is moved away. This is accomplished as noted below.

The pen 55 is mounted on arm 57 pivotally connected to the cross arm 58 by pivot 59. A spring 60 normally urges the arm 57 upwardly so that the pen 55 is out of engagement with the chart paper 56. A solenoid 62 is energized during a test via the circuit which includes the specimen and pulls the arm 57 down so that the pen 55 is against the chart paper 56. At the point of rupture, the solenoid is de-energized and the spring 60 causes the pen to disengage from the chart paper 56 and terminate the tracing.

I will now describe the other important features of the invention, that is to say the improved extensometer having automatic gauge length setting.

The extensometer comprises a pair of upright standards 63 and 64, a strain cradle 65, and means mounting the strain followers 11 and 12.

The standards 63 and 64 are each fixed to the base 16, for example, as by bracket 66 for the standard 63.

The strain cradle 65 includes a pair of end pieces 70 and 71, a tie-in angle 72 fixed to the end pieces, a position bar 73 fixed to the end pieces, and an air bearing shaft 74 including pivots 75 and 76 by which the cradle is rotatably mounted on the standards 63 and 64. The cradle rotates about the axis of the air bearing shaft 74.

The cradle is rotated by a piston/cylinder means, the cylinder 80 being pivotally connected to the lower end of the end piece 70 by pivot 81 and the piston inside the cylinder having a rod 82 which is pivotally connected to the upright 63 by the pivot 83.

In FIG. 5, the cradle 65 is shown in its operative position. The position is determined by the engagement of the screws 84 on the standard 63 and the lower end 70a of the end piece 70. The screw is adjustably mounted in the nut 85 which is secured to standard 63. When the cylinder 80 is moved down on the rod 82, the cradle is rotated counterclockwise to an inoperative position which is determined by the piston bottoming the end of the cylinder.

The air bearing shaft 74 mounts a pair of air bearings 86 and 87 which float on a band of air around the shaft 74 and are essentially friction free. The air bearings can move in a direction along the shaft and also rotate about the axis of the shaft. The air tubes 90 and 91 are each helically wound around the shaft and are connected to a source of air. The helical shape has a permanent set in order to prevent restriction in air supply. This is done by using tubes of thermo plastic material, heating and then cooling while in the helical form.

The air bearings 86 and 87 are arranged to be rotated with the cradle 65 as between the operative and inoperative positions. This is accomplished by the position brackets 92 and 93 respectively connected to the air bearings 86 and 87. Each position bracket has a clearance opening through which extends the position bar 73. Each clearance opening is dimensioned so that when the strain cradle 65 is in the operative position, the position bracket is free on the openings. Thus, the position brackets can move with air bearing without imposing friction loads. Also, it will be evident that when the cradle 65 is rotated as between operative and inoperative positions the bar 73 will engage the side of the openings and, thus, rotate the air bearings 86 and 87 with the cradle.

The strain followers 11 and 12 are connected to the air bearings 86 and 87 as by the strain follower arms 94 and 95 carrying weights 96 and 97 which can be adjustably positioned along the respective arms.

In FIGS. 7 and 8 the strain cradle 65 has been rotated to the operative position and the follower arms 94 and 95 rotate down with the air bearings bringing the strain followers 11 and 12 into engagement with specimen S. When the strain cradle 65 is rotated to the inoperative position, the strain followers 11 and 12 move away from and out of contact with the specimen.

The strain followers 11 and 12 are of identical construction. As noted for the follower 11, this includes a disc-like body 100 having a peripheral groove which supports an annular or double round ring 101 made of yieldable matter such as rubber. The ring makes a frictional engagement with the specimen S and the engagement will cause the followers to move apart as the specimen strains. This movement, of course, results in corresponding movement in the follower arms 94 and 95 and of the air bearings 86 and 87. The engagement force of the followers 11 and 12 with the specimen is determined by the position of weights 96 and 97.

The double round structure of ring 101 is important because the contact with the specimen is a finite point. The area of the point of contact is determined by the choice of material of the ring 101 and the location of the weights 96 and 97.

The means on the extensometer for quickly and accurately determining the specimen gauge length will now be described.

The air bearings 86 and 87 respectively have the gauge followers 102 and 103 connected thereto. The gauge followers 102 and 103 are respectively provided with peripheral concave grooves 104 and 105.

A cam means 106 is arranged to move toward the axis of the air bearing shaft 74 to engage with the groove 104 and then to move away from the axis to disengage from the groove 104 while a cam means 107 is arranged to move toward the axis of the shaft 74 to engage with an L-shaped groove 105 and then move away from the axis to disengage from the groove 105. To achieve the foregoing motion of the gauge cams 106 and 107 the same are mounted on cam frame 110 which is described below.

Referring to FIG. 7, the bracket 111 is connected to the tie-in angle 72 by the clamp 112. The cam frame 110 slidably rests on the retainer foot 113 of the bracket 111. A piston/cylinder is used to move the cam frame 110, the cylinder 114 being mounted on the bracket 111 and the piston in the cylinder having a rod 115 connected to the cam frame 110.

It will be apparent that when the cams 106 and 107 are moved inwardly the same will respectively contact the grooves 104 and 106. If the followers 102 and 103 are spread apart to a greater extent than is shown in FIG. 8, the cams will move the followers into the position shown. This positions the strain followers 11 and 12 a known distance apart; i.e. establishing the gauge length.

Normally, the gauge length is set while the strain cradle 65 is in the inoperative position and the cams 106 and 107 maintained in contact with the follower grooves 102 and 103 until the cradle is in the operative position with the strain followers 11 and 12 engaging the specimen S. At that time, the cams are moved away from the grooves so that the strain followers 11 and 12 are free to sense the specimen strain during a test.

In the embodiment described herein, the amount of motion of the air bearings, hence the amount of specimen strain, is sensed by a transducer means 120 which is a conventional LVDT having coil and core elements. The housing 121 for the coil is supported by the arm 122 secured to the air bearing 86 and the core rod 123 is connected by arm 124 to air bearing 87.

The transducer 120 is employed for specimens where the magnitude of strain is relatively short. In the cases where specimens are of the type where strain magnitudes are substantial, other transducers are employed. A typical machine and extensometer for specimens where strain magnitudes are substantial is shown in U.S. Pat. No. 3,835,699 assigned to the Assignee of this application.

Before closing it is pointed out that after a test is completed the relative position of the air bearings is adjusted either manually or automatically to get ready for the next test. This normally is done with the cradle 65 is the inoperative position. To prevent over-run of the air bearings 86 (and its strain follower lower 11), a stop 125 (FIG. 4) is appropriately positioned on the position bar 73. Also, the elements 92a and 93a are magnetic donuts employed in a large strain measuring system.

I claim:

1. In a horizontal tensile testing machine, an improved extensometer means for determining the strain of specimens subjected to tensile forces:

a pair of spaced apart, upwardly extending standards;

a horizontally extending air bearing support shaft connected between the standards, the standards being adapted to position the shaft generally parallel the axis of a specimen to be tested;

a pair of air bearings mounted on said air bearing support shaft for movement along the axis of the air bearing support shaft and for rotation about the axis of the shaft;

a pair of strain followers respectively connected to said air bearings for movement therewith, each strain follower having means to engage the specimen, the engagement being frictional, and non-penetrating;

sensing means connected between the air bearings for use in sensing the relative positions of the air bearings along the air bearing support shaft and, therefore, the relative positions of the strain followers in a direction parallel the axis of a specimen to be tested;

strain cradle means extending between said standards;

means mounting the strain cradle means for rotation about the axis of the air bearing support shaft and the strain cradle means having a position bar extending parallel the air bearing support shaft;

means to rotate the strain cradle means as between an operative and an inoperative position;

a pair of position brackets respectively connected to said air bearings and each having a clearance opening through which extends the position bar, the clearance openings providing freedom for the air bearings to move along the axis of the air bearing support shaft and also providing for the position brackets to be engaged by the position bar so as to rotate the strain followers with the strain cradle;

said operative position being adapted to position the strain followers in contact with a specimen to be tested so as to relatively move in accordance with specimen strain and thereby cause relative motion of the air bearings along the air bearing support shaft and said inoperative position being adapted to position the strain followers away from and out of contact with a specimen to be tested;

a pair of gauge cams, the gauge cams being spaced a fixed distance apart;

a pair of gauge followers respectively connected to said air bearings for movement therewith, each gauge follower having an exterior concave groove; and means supporting each gauge cam on said strain cradle for reciprocating motion toward and away from the axis of the air bearing support shaft to respectively engage with and disengage from the exterior concave grooves of the gauge followers, the engagements between the concave grooves and the gauge cams being for use in establishing the gauge length of said strain followers.

2. The extensometer of claim 1 wherein said sensing means comprises:

a transducer having a core element and a coil element; and means connecting the coil element with one of said air bearings and means connecting the core element with the other air bearing.

3. The extensometer of claim 1 wherein:

a tie-in bracket is connected between said standards;
the gauge cams are mounted on a common frame; and
the means supporting the gauge followers comprises bracket means connected to the tie-in angle, a piston and cylinder means, the cylinder being connected to the bracket and the piston being connected to the common frame.

4. The extensometer of claim 1 wherein the means to engage the specimen on each strain follower being in the form of a double round ring made of material which makes a frictional engagement with the specimen.

5. In a testing machine having an extensometer including a pair of strain followers, improved means for setting the gauge length of the strain followers:

a pair of gauge followers respectively connected to the strain followers and each gauge follower having an exterior concave groove;
a pair of gauge cams; and
means supporting the gauge cams a fixed distance apart and for a reciprocating motion toward and away from the gauge followers to respectively engage with and to disengage from the exterior concave grooves, the engagements being for use in establishing the gauge length of the strain followers.

* * * * *